(12) United States Patent
Crapser et al.

(10) Patent No.: US 7,368,003 B2
(45) Date of Patent: May 6, 2008

(54) SYSTEMS FOR AND METHODS OF PROVIDING AIR PURIFICATION IN COMBINATION WITH ODOR ELIMINATION

(75) Inventors: James R. Crapser, Racine, WI (US); Milan L. Zdrubecky, Milwaukee, WI (US); René Maurice Béland, Waterford, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 214 days.

(21) Appl. No.: 11/166,588

(22) Filed: Jun. 24, 2005

(65) Prior Publication Data

US 2006/0288871 A1   Dec. 28, 2006

(51) Int. Cl.
   *B03C 3/019*   (2006.01)
(52) U.S. Cl. .................... 96/52; 95/58; 95/63; 95/71; 96/53; 96/63; 96/74; 96/222; 261/DIG. 88
(58) Field of Classification Search ............ 96/52, 96/53, 63, 74, 222; 95/58, 63, 64, 71; 261/DIG. 88, 261/DIG. 17, DIG. 89
See application file for complete search history.

(56) References Cited

U.S. PATENT DOCUMENTS

| | | | |
|---|---|---|---|
| 912,106 A | 2/1909 | Frazier |
| 1,372,251 A | 3/1921 | Schnee |
| 2,044,832 A | 6/1936 | Child |
| 2,065,970 A | 12/1936 | Hartzell |
| 2,335,056 A | 11/1943 | Grison |
| 2,528,301 A | 10/1950 | Doe |
| 2,611,068 A | 9/1952 | Wellens |
| 2,638,644 A | 5/1953 | Rauhut |
| 2,746,416 A | 5/1956 | Aufderheide |
| 2,825,318 A | 3/1958 | Mansfield |
| D189,420 S | 12/1960 | Diehl |
| 3,297,209 A | 1/1967 | Punaitore |
| 3,458,794 A | 7/1969 | Bohnstedt et al. |
| 3,474,376 A | 10/1969 | Preiss |
| D216,794 S | 3/1970 | Patrick |
| 3,600,590 A | 8/1971 | Einstein |
| 3,624,161 A | 11/1971 | Bub |
| 3,745,750 A | 7/1973 | Arff |
| 3,757,495 A | 9/1973 | Seivers |
| 3,776,177 A | 12/1973 | Bryant et al. |
| 3,860,404 A | 1/1975 | Jochimski |
| 3,860,818 A | 1/1975 | Stalder et al. |
| D234,606 S | 3/1975 | Gamble |
| 3,873,835 A | 3/1975 | Ignatiev |
| 3,921,568 A | 11/1975 | Fish |
| 3,923,934 A | 12/1975 | Watkins |

(Continued)

FOREIGN PATENT DOCUMENTS

EP   0 693 659 A2   1/1996

(Continued)

*Primary Examiner*—Richard L. Chiesa

(57) ABSTRACT

Systems for and methods of providing air purification and cleaning in combination with odor elimination in a single unit, such as a tabletop unit for home or office use, are disclosed. The air cleaning device includes a housing, an air intake port, an air movement mechanism, a pre-ionizer, a filter, a post-ionizer, an air exhaust port, and a flow chamber for holding a compound such as an odor elimination supply. An air movement mechanism, ozone removal mechanism, and/or filter/odor elimination assembly may also be present.

17 Claims, 9 Drawing Sheets

U.S. PATENT DOCUMENTS

| | | |
|---|---|---|
| 3,936,284 A | 2/1976 | Mason |
| 3,948,445 A | 4/1976 | Andeweg |
| 4,004,361 A | 1/1977 | McVeety |
| 4,006,841 A | 2/1977 | Alticosalian |
| 4,040,568 A | 8/1977 | Mason, Jr. et al. |
| 4,043,776 A | 8/1977 | Orel |
| 4,059,422 A | 11/1977 | Steiner |
| 4,118,191 A | 10/1978 | Bohnensieker |
| 4,121,529 A | 10/1978 | Smith et al. |
| 4,121,916 A | 10/1978 | Fricke |
| 4,173,995 A | 11/1979 | Beck |
| 4,177,045 A | 12/1979 | Orel |
| 4,210,429 A | 7/1980 | Gostein |
| 4,214,146 A | 7/1980 | Schimanski |
| 4,214,882 A | 7/1980 | Brenholt |
| 4,219,531 A | 8/1980 | Wisniewski |
| 4,244,710 A * | 1/1981 | Burger ................ 95/69 |
| 4,272,261 A | 6/1981 | Lynch, Jr. et al. |
| 4,301,095 A | 11/1981 | Mettler et al. |
| 4,317,661 A | 3/1982 | Sasaoka et al. |
| 4,344,776 A | 8/1982 | Yavnelli |
| 4,467,263 A | 8/1984 | Conforti et al. |
| 4,597,781 A * | 7/1986 | Spector ................ 96/52 |
| 4,605,425 A | 8/1986 | Verrando et al. |
| 4,629,482 A | 12/1986 | Davis |
| 4,647,831 A | 3/1987 | O'Malley et al. |
| 4,666,638 A | 5/1987 | Baker et al. |
| 4,694,142 A | 9/1987 | Glucksman |
| 4,701,195 A | 10/1987 | Rosendall |
| 4,711,161 A | 12/1987 | Swin, Sr. et al. |
| 4,719,662 A | 1/1988 | Horak et al. |
| 4,731,520 A | 3/1988 | Glucksman et al. |
| D295,217 S | 4/1988 | Glucksman |
| 4,737,173 A | 4/1988 | Kudirka et al. |
| 4,743,406 A | 5/1988 | Steiner et al. |
| 4,743,829 A | 5/1988 | Fenne et al. |
| D296,468 S | 6/1988 | Greubel |
| 4,792,345 A | 12/1988 | Abe et al. |
| 4,795,883 A | 1/1989 | Glucksman et al. |
| 4,804,821 A | 2/1989 | Glucksman |
| 4,830,791 A | 5/1989 | Muderlak et al. |
| 4,839,014 A | 6/1989 | Park et al. |
| 4,849,862 A | 7/1989 | Diskin et al. |
| 4,859,220 A | 8/1989 | Leber et al. |
| 4,873,422 A | 10/1989 | Streich et al. |
| D305,260 S | 12/1989 | Mito |
| D307,050 S | 4/1990 | Glucksman et al. |
| 4,917,862 A | 4/1990 | Kraw et al. |
| 4,919,693 A | 4/1990 | Olney |
| 4,931,224 A | 6/1990 | Holzner, Sr. |
| 4,937,912 A | 7/1990 | Kurz |
| 4,942,841 A | 7/1990 | Drucker, Jr. |
| 4,973,827 A | 11/1990 | Nozaki |
| 4,986,901 A | 1/1991 | Nohren, Jr. et al. |
| 4,997,381 A | 3/1991 | Oh |
| 5,006,779 A | 4/1991 | Fenne et al. |
| 5,014,338 A | 5/1991 | Glucksman |
| 5,019,352 A * | 5/1991 | Gonzalez ................ 96/222 |
| 5,035,728 A | 7/1991 | Fang |
| 5,036,698 A | 8/1991 | Conti |
| 5,038,394 A | 8/1991 | Hasegawa et al. |
| 5,061,296 A | 10/1991 | Sengpiel et al. |
| 5,089,144 A | 2/1992 | Ozkahyaoglu et al. |
| 5,089,202 A | 2/1992 | Lippold |
| D325,253 S | 4/1992 | Muderlak |
| 5,111,477 A | 5/1992 | Muderlak et al. |
| 5,111,529 A | 5/1992 | Glucksman |
| 5,112,370 A | 5/1992 | Gazzano |
| 5,131,932 A | 7/1992 | Glucksman |
| 5,133,788 A | 7/1992 | Backus |
| D328,637 S | 8/1992 | Muller et al. |
| 5,139,546 A | 8/1992 | Novobilski |
| 5,160,879 A | 11/1992 | Tortola et al. |
| 5,163,202 A | 11/1992 | Kawakami et al. |
| 5,192,342 A | 3/1993 | Baron et al. |
| 5,210,818 A | 5/1993 | Wang |
| 5,220,152 A | 6/1993 | Doran |
| 5,220,636 A | 6/1993 | Chang |
| 5,230,723 A | 7/1993 | Travis et al. |
| D338,521 S | 8/1993 | Ganor |
| D338,709 S | 8/1993 | Lin |
| 5,236,477 A | 8/1993 | Koketsu |
| 5,239,610 A | 8/1993 | Shao |
| 5,240,478 A | 8/1993 | Messina |
| 5,250,232 A | 10/1993 | Pepper et al. |
| 5,266,004 A | 11/1993 | Tsumurai et al. |
| D345,010 S | 3/1994 | Aronsson et al. |
| 5,290,546 A | 3/1994 | Hasegawa et al. |
| 5,330,722 A | 7/1994 | Pick et al. |
| 5,332,425 A | 7/1994 | Huang |
| 5,377,614 A | 1/1995 | Glazer |
| 5,378,254 A | 1/1995 | Maly et al. |
| 5,401,178 A | 3/1995 | Liu |
| D357,330 S | 4/1995 | Wong et al. |
| 5,407,469 A | 4/1995 | Sun |
| D360,028 S | 7/1995 | Matsuda |
| 5,435,817 A | 7/1995 | Davis et al. |
| 5,474,600 A | 12/1995 | Volodina et al. |
| 5,494,449 A | 2/1996 | Chioo |
| D371,192 S | 6/1996 | Putro |
| 5,547,615 A | 8/1996 | Jane et al. |
| 5,554,039 A | 9/1996 | Doudon |
| D374,278 S | 10/1996 | Ganor |
| D374,713 S | 10/1996 | Ford et al. |
| D377,213 S | 1/1997 | Wang |
| 5,601,636 A | 2/1997 | Glucksman |
| 5,611,967 A | 3/1997 | Jane et al. |
| 5,613,863 A | 3/1997 | Klaus et al. |
| 5,616,172 A | 4/1997 | Tuckerman et al. |
| D379,220 S | 5/1997 | Ellwood |
| 5,628,641 A | 5/1997 | Hahn |
| 5,634,806 A | 6/1997 | Hahn |
| 5,679,137 A | 10/1997 | Erdman et al. |
| 5,681,630 A | 10/1997 | Smick et al. |
| D388,510 S | 12/1997 | Rick et al. |
| D390,940 S | 2/1998 | Chen |
| 5,713,749 A | 2/1998 | Wu |
| 5,735,918 A | 4/1998 | Barradas |
| 5,741,352 A | 4/1998 | Ford et al. |
| D394,100 S | 5/1998 | Promseeda |
| D395,146 S | 6/1998 | Miller et al. |
| 5,762,667 A | 6/1998 | Pippel et al. |
| 5,769,912 A | 6/1998 | Mansur |
| 5,772,732 A | 6/1998 | James et al. |
| D396,275 S | 7/1998 | Pearson |
| 5,783,117 A | 7/1998 | Byassee et al. |
| 5,791,921 A | 8/1998 | Lee |
| 5,792,230 A | 8/1998 | Moore et al. |
| 5,800,583 A | 9/1998 | Pippel et al. |
| 5,800,741 A | 9/1998 | Glenn et al. |
| 5,803,940 A | 9/1998 | Rick et al. |
| 5,810,908 A | 9/1998 | Gray et al. |
| 5,811,004 A | 9/1998 | Robertson |
| D399,943 S | 10/1998 | Ko |
| 5,819,367 A | 10/1998 | Imamura |
| D400,661 S | 11/1998 | Ko |
| D400,662 S | 11/1998 | Davis |
| 5,829,993 A | 11/1998 | Wu |
| 5,837,207 A | 11/1998 | Summers |
| 5,840,092 A | 11/1998 | Rick et al. |
| 5,840,094 A | 11/1998 | Osendorf et al. |
| D402,022 S | 12/1998 | Termeer et al. |
| 5,862,737 A | 1/1999 | Chiu et al. |
| 5,879,435 A | 3/1999 | Satyapal et al. |

| | | | | | | |
|---|---|---|---|---|---|---|
| 5,891,399 | A | 4/1999 | Owesen | 6,645,266 | B2 | 11/2003 | Huang |
| D409,741 | S | 5/1999 | Yuen-Ming | D485,340 | S | 1/2004 | Wu |
| 5,906,509 | A | 5/1999 | Wu | 6,709,297 | B2 | 3/2004 | Lee |
| D411,001 | S | 6/1999 | Pinchuk | 6,712,889 | B2 | 3/2004 | Pillion et al. |
| 5,914,453 | A | 6/1999 | James et al. | 6,713,026 | B2 | 3/2004 | Taylor et al. |
| 5,925,172 | A | 7/1999 | Rick et al. | 6,749,654 | B2 | 6/2004 | Hilliard |
| 5,925,320 | A | 7/1999 | Jones | 6,757,150 | B2 | 6/2004 | Gorczyca et al. |
| 5,926,614 | A | 7/1999 | Steinel | 6,758,884 | B2 | 7/2004 | Zhang et al. |
| 5,945,038 | A | 8/1999 | Anderson | 6,768,865 | B2 | 7/2004 | Stathakis et al. |
| 5,948,355 | A | 9/1999 | Fujishima et al. | 6,790,259 | B2 | 9/2004 | Ritri et al. |
| 5,957,701 | A | 9/1999 | McMillin | 6,862,403 | B2 | 3/2005 | Pedrotti et al. |
| 5,967,807 | A | 10/1999 | Wu | 6,863,703 | B2 | 3/2005 | Pillion et al. |
| 5,968,455 | A | 10/1999 | Brickley | 6,863,704 | B2 | 3/2005 | Pillion et al. |
| D416,318 | S | 11/1999 | Sato | 6,886,814 | B1 | 5/2005 | Schuld |
| D416,319 | S | 11/1999 | Rollins | 6,887,299 | B2 * | 5/2005 | Weigl ............... 95/26 |
| D416,613 | S | 11/1999 | Bellil et al. | 6,896,853 | B2 | 5/2005 | Lau et al. |
| 5,986,555 | A | 11/1999 | Hamberger et al. | 6,897,381 | B2 | 5/2005 | He et al. |
| 5,997,619 | A | 12/1999 | Knuth et al. | 6,911,186 | B2 | 6/2005 | Taylor et al. |
| 6,013,121 | A | 1/2000 | Chiu et al. | 6,917,754 | B2 | 7/2005 | Pedrotti et al. |
| 6,017,375 | A | 1/2000 | Duell et al. | 6,931,202 | B2 | 8/2005 | Pedrotti et al. |
| D420,732 | S | 2/2000 | Gudefin | 6,951,582 | B1 | 10/2005 | Tsai et al. |
| 6,036,757 | A | 3/2000 | Gatchell et al. | 6,953,556 | B2 | 10/2005 | Taylor et al. |
| 6,042,400 | A | 3/2000 | Queffelec et al. | 6,955,708 | B2 | 10/2005 | Julos et al. |
| 6,045,596 | A | 4/2000 | Holland, Jr. et al. | 6,958,134 | B2 | 10/2005 | Taylor et al. |
| 6,051,144 | A | 4/2000 | Clack et al. | 6,974,560 | B2 | 12/2005 | Taylor |
| 6,053,482 | A | 4/2000 | Glenn et al. | 6,989,051 | B2 | 1/2006 | Parisi et al. |
| 6,053,968 | A | 4/2000 | Miller | 7,025,798 | B2 * | 4/2006 | Endo ............... 55/385.1 |
| 6,059,584 | A | 5/2000 | Mareno | 7,045,000 | B2 * | 5/2006 | Kim ................ 96/222 |
| 6,062,880 | A | 5/2000 | Skuza | 2001/0029728 | A1 | 10/2001 | Massey et al. |
| 6,062,884 | A | 5/2000 | Messimer et al. | 2001/0045159 | A1 | 11/2001 | Johnson et al. |
| D426,293 | S | 6/2000 | Tounsi et al. | 2002/0098130 | A1 | 7/2002 | Hai Fong |
| 6,089,886 | A | 7/2000 | Mareno | 2002/0139251 | A1 * | 10/2002 | Simmons ............ 96/134 |
| D428,862 | S | 8/2000 | Queffelec et al. | 2002/0146356 | A1 | 10/2002 | Sinaiko |
| D432,222 | S | 10/2000 | Rymer et al. | 2003/0019362 | A1 | 1/2003 | Stiros et al. |
| 6,126,460 | A | 10/2000 | Wu | 2003/0029319 | A1 * | 2/2003 | Ninomiya et al. .......... 96/63 |
| D433,493 | S | 11/2000 | Runyan et al. | 2004/0065202 | A1 | 4/2004 | Gatchell et al. |
| D434,483 | S | 11/2000 | Pinchuk | 2004/0065749 | A1 * | 4/2004 | Kotary et al. ............ 239/44 |
| 6,163,098 | A | 12/2000 | Taylor et al. | 2004/0118285 | A1 | 6/2004 | Kim et al. |
| 6,174,342 | B1 | 1/2001 | Jeanseau | 2004/0129140 | A1 | 7/2004 | Park et al. |
| 6,176,977 | B1 | 1/2001 | Taylor et al. | 2004/0163542 | A1 * | 8/2004 | Huang ................ 96/222 |
| 6,179,633 | B1 | 1/2001 | Inada | 2004/0222315 | A1 | 11/2004 | Habatiou |
| 6,190,184 | B1 | 2/2001 | Cimbal et al. | 2005/0081719 | A1 * | 4/2005 | Carlsson ............. 96/223 |
| 6,190,442 | B1 | 2/2001 | Redner | 2005/0109204 | A1 | 5/2005 | Coppom et al. |
| 6,225,907 | B1 | 5/2001 | Derryberry et al. | 2005/0160907 | A1 | 7/2005 | Zhang et al. |
| 6,239,694 | B1 | 5/2001 | Honda et al. | 2005/0183576 | A1 | 8/2005 | Taylor et al. |
| D450,377 | S | 11/2001 | Terpko et al. | 2005/0223893 | A1 | 10/2005 | Hoverson et al. |
| 6,312,507 | B1 * | 11/2001 | Taylor et al. .......... 96/19 | 2006/0000359 | A1 | 1/2006 | Choi et al. |
| 6,315,821 | B1 | 11/2001 | Pillion et al. | 2006/0016335 | A1 | 1/2006 | Cox et al. |
| 6,328,791 | B1 | 12/2001 | Pillion et al. | 2006/0016336 | A1 | 1/2006 | Taylor et al. |
| 6,349,168 | B1 | 2/2002 | Jaworski | 2006/0016337 | A1 | 1/2006 | Taylor et al. |
| D456,070 | S | 4/2002 | Garman | 2006/0021503 | A1 | 2/2006 | Thaler |
| 6,364,716 | B1 | 4/2002 | Seo | 2006/0032199 | A1 | 2/2006 | Beam et al. |
| D457,230 | S | 5/2002 | Huang | 2006/0045036 | A1 | 3/2006 | Vetter et al. |
| 6,413,302 | B1 | 7/2002 | Harrison et al. | 2006/0053758 | A1 | 3/2006 | Wu et al. |
| 6,447,587 | B1 | 9/2002 | Pillion et al. | 2006/0075729 | A1 | 4/2006 | He et al. |
| 6,454,839 | B1 | 9/2002 | Hagglund et al. | 2006/0130657 | A1 | 6/2006 | Bohlen et al. |
| D464,415 | S | 10/2002 | Saunders et al. | | | | |
| D465,019 | S | 10/2002 | Wu | | | | |
| 6,471,746 | B2 | 10/2002 | Hagglund et al. | | | | |
| 6,471,752 | B1 | 10/2002 | Lewis | | | | |
| D465,275 | S | 11/2002 | Gaman | | | | |
| D468,820 | S | 1/2003 | Smith et al. | | | | |
| 6,508,868 | B2 | 1/2003 | Pillion et al. | | | | |
| 6,540,804 | B1 | 4/2003 | Wennerstrom | | | | |
| 6,544,485 | B1 | 4/2003 | Taylor | | | | |
| 6,568,662 | B2 | 5/2003 | Schuld | | | | |
| D476,068 | S | 6/2003 | Carey et al. | | | | |
| 6,579,333 | B2 | 6/2003 | Huang | | | | |
| 6,589,317 | B2 | 7/2003 | Zhang et al. | | | | |
| 6,610,121 | B2 * | 8/2003 | Chasen ............... 95/1 | | | | |
| 6,616,736 | B2 | 9/2003 | Massey et al. | | | | |
| 6,632,407 | B1 | 10/2003 | Lau et al. | | | | |
| 6,635,106 | B2 | 10/2003 | Katou et al. | | | | |

FOREIGN PATENT DOCUMENTS

| | | | |
|---|---|---|---|
| EP | 1245289 | A2 | 10/2002 |
| EP | 1447629 | A | 8/2004 |
| FR | 02689399 | A1 | 10/1993 |
| GB | 2036951 | A * | 7/1980 ................ 96/222 |
| GB | 2088250 | A | 6/1982 |
| JP | 46-599 | | 1/1971 |
| JP | 53-130578 | | 11/1978 |
| JP | 54-162660 | | 12/1979 |
| JP | 58-166948 | | 10/1983 |
| JP | 60-174439 | | 9/1985 |
| JP | 61135821 | | 6/1986 |
| JP | 61-163351 | | 7/1986 |
| JP | 62-68513 | | 3/1987 |
| JP | 63-258615 | | 4/1987 |

| | | |
|---|---|---|
| JP | 63-137718 | 6/1988 |
| JP | 63-205114 | 8/1988 |
| JP | 11-76726 | 7/1989 |
| JP | 3-254808 | 11/1991 |
| JP | 4-149885 | 5/1992 |
| JP | 6-39226 | 2/1994 |
| JP | 8-131742 | 5/1996 |
| WO | WO 97/47928 A2 | 12/1997 |
| WO | WO 97/47928 A3 | 12/1997 |
| WO | WO 98/29695 | 7/1998 |
| WO | WO 99/03158 A1 | 1/1999 |
| WO | WO 2004/047877 A2 | 6/2004 |
| WO | WO 2005/039659 | 5/2005 |
| WO | WO 2006/023796 | 3/2006 |
| WO | WO 2006/051267 | 5/2006 |

* cited by examiner

SYSTEMS FOR AND METHODS OF PROVIDING AIR PURIFICATION IN COMBINATION WITH ODOR ELIMINATION

BACKGROUND OF THE INVENTION

1. Field of the Invention

The present invention relates to air cleaning devices. In particular, this invention relates to air cleaning devices that provide air purification in combination with odor elimination.

2. Discussion of the Related Art

The increase of outdoor air pollution over many years has created a greater awareness for the type of damage that outdoor air pollution can cause to one's health. What is not commonly known, however, is that indoor air pollution also exists and can have a significant affect on one's health. There have been recent Environmental Protection Agency studies that indicate that indoor air pollution levels have the potential to be 2-5 times higher than outdoor air pollution levels. It is estimated by some that, on rare occasions, indoor air pollution levels can be 100 times higher than outdoor air pollution levels. This is an increasingly important matter that must be addressed, as some people spend 90% of their time indoors, especially infants and the elderly. Some of these indoor pollutants may also be contributing factors to frequent and unexplained headaches or sleepless nights that afflict numerous persons within the general population.

There have been numerous prior art apparatuses designed and manufactured for purifying air. With more homes and offices becoming better insulated, an objective of air purifiers is to clear the indoor air of common pollutants, including dust, smoke, pollen, bacteria, soot, mold spores, animal dander and other microscopic irritants, and thereby create a clean, healthy, fresh, and pleasant environment. Some of these apparatuses generate ions by using complicated wire grid arrays or with high voltage electrode arrays. Some use fans for moving air and similar complicated apparatuses. Some of these prior art devices are mounted in large housings that contain fans and other complicated moving parts and filters. Often, they become clogged with pollutants, requiring disassembly of fan assemblies, replacement and/or repair of high-voltage generating sources, extensive clearing of arrays of wires and electrodes that help create air movement, and replacement of filters that clog the apparatuses unless cleaned. These devices are certainly more complicated and perhaps more expensive than what some users may anticipate or desire.

Another aspect of air cleaning that is of interest to consumers is that of adding a component that eliminates odors. However, air cleaning devices are typically only odor modifiers because they employ volatile fragrance agents for masking odors rather than employing odor elimination (OE) compounds for removing odors. What is needed is an effective air purification device that includes an odor elimination mechanism.

Furthermore, air cleaning devices were initially used in bathrooms and kitchens and, consequently, have tended to be more functional than attractive. Air cleaning devices are now used in bedrooms and living rooms, and consumers who wish to use air fresheners in these areas of the home may be reluctant to place an unattractive, functional container in these areas. Furthermore, what is needed is a way of providing a combination of air purification and odor elimination in a single air cleaning device, such as a portable tabletop device.

Odor elimination compounds, such as provided by Givaudan Fragrances Corp. (Mount Olive, N.J.) and Quest International (Netherlands), may include a fragrance element that serves to impart a pleasant odor to the room as well as to indicate to the consumer that the odor elimination compound is working. Additionally, it is desirable for a consumer to have a choice of fragrances within a single air cleaning device and, therefore, eliminate the inconvenience of having to manually remove and replace the fragrance supply each time a different fragrance is desired. Alternatively, an odor elimination compound may be a volatile that reacts with the odor causing molecule. What is needed is a way of providing multiple odor elimination compounds with fragrance element in a single air cleaning device.

Additionally, because the intensity of odors in a home may vary throughout the day, for example, at mealtime cooking odors are stronger than at non-mealtimes, it is beneficial to be able to vary the odor elimination level provided by an air cleaning device. What is needed is a way of providing the ability to adjust the odor elimination level in an air cleaning device.

For years ozone has been used to treat and sanitize water supplies, sanitize pools and spas and remove odors in hotels and fire-damaged buildings. More recently ozone generators have been sold as a way to "clean" the air in a home. Ozone is a molecule formed of three atoms of oxygen. As an unstable molecule, ozone readily offers one of the oxygen atoms to other substances it encounters. When ozone encounters another substance, it shares an oxygen atom, chemically altering that substance. The chemical alteration of micro-organisms, mold, mildew, fungi and bacteria generally results in the death of those substances and the elimination of its odor. Manufacturers of ozone generators and public health agencies are engaged in debate over the use of ozone in the home. Public health agencies claim that ozone is potentially dangerous to human health and recommend that the generators not be used, as ozone may be a respiratory irritant. The same chemical properties that allow ozone to react with organic material in the air also allow it to react with similar organic material inside the human body, particularly in the respiratory system. While most people can stand limited exposure, symptoms like mouth and throat dryness, coughing, headache, eye irritation and chest restriction may occur in some individuals at the concentrations produced by residential ozone generators. Moreover, consumers generally do not want a "one size fits all" air cleaning device. Consumers prefer an air cleaning device that can be customized to meet their specific needs. Consequently, to overcome the limitations of air cleaning devices that are currently available on the market and to address a wide range of consumer needs. Therefore, what is needed is a way of providing an effective air purification device that includes an ozone reducing mechanism and a way re-configuring the device to meet a specific consumer's needs.

SUMMARY OF THE INVENTION

A preferred embodiment of the invention has one or more of the following features:

an effective air purification device that includes an odor elimination mechanism;

a combination of air purification and odor elimination in a single air cleaning device;

multiple odor elimination compounds with fragrance element in a single air cleaning device;

the ability to adjust the air flow and odor elimination level in an air cleaning device;

an effective air purification device that includes an ozone reducing mechanism; and a filter unit that contains a odor elimination dispersion mechanism.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

DETAILED DESCRIPTION OF THE PREFERRED EMBODIMENT

The present invention includes systems for and methods of providing air purification preferably in combination with odor elimination in a single air cleaning unit, such as a tabletop unit for home or office use. More specifically, an air cleaning device of the present invention generally provides an odor elimination treatment to a room by preferably entering at least one an odor elimination compound into the filtered air exhaust stream of the device. Certain embodiments of the air cleaning device of the present invention provide the user a mechanism for selecting one of multiple odor elimination compounds and the ability to adjust the odor elimination level. Certain embodiments of the air cleaning device of the present invention also provide air purification in combination with an ozone reducing mechanism.

Figure 1:
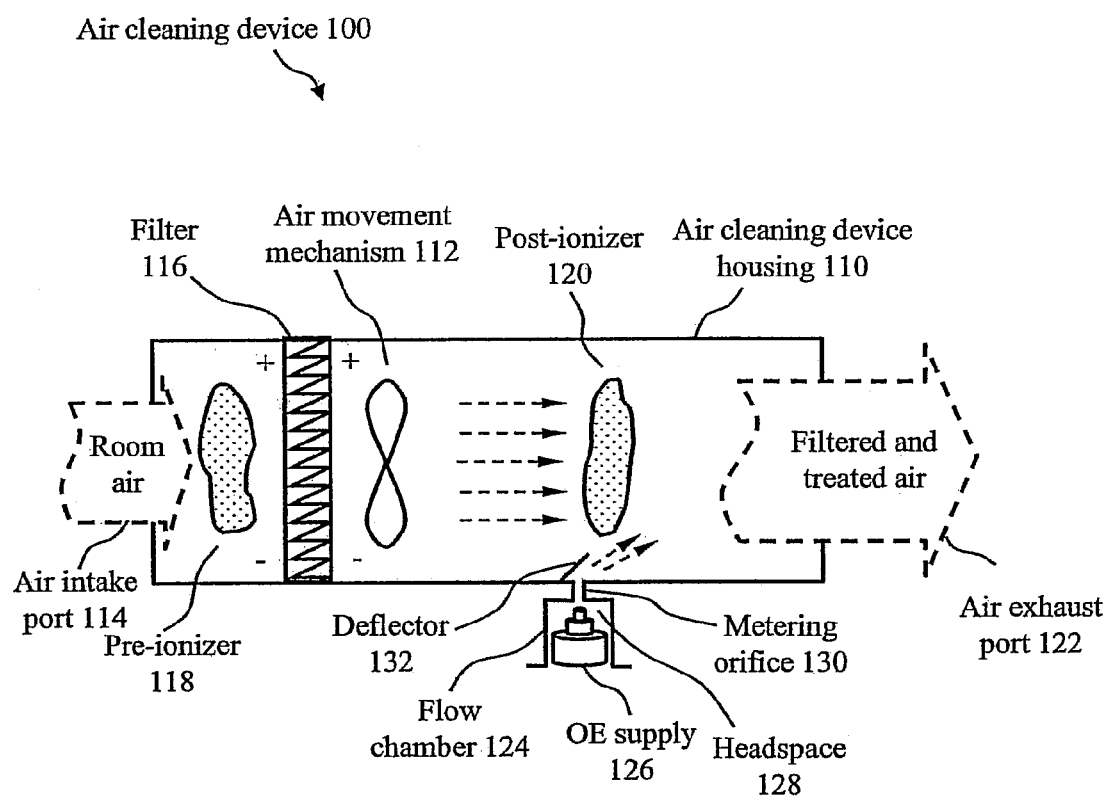
FIG. 1 is a functional diagram of an air cleaning device that provides air purification in combination with odor elimination in accordance with a first embodiment of the invention.

FIG. 1 is a functional diagram of an air cleaning device 100 that provides air purification preferably in combination with odor elimination in accordance with a first embodiment of the invention. Air cleaning device 100 of the present invention generally provides an odor elimination treatment to a room preferably by entering an odor elimination compound into the filtered air exhaust stream of the device.

Air cleaning device preferably 100 includes an air cleaning device housing 110, within which is installed an air movement mechanism 112 for drawing airflow into air cleaning device housing 110 via an air intake port 114. Airflow generated by air movement mechanism 112 moves air against and through a filter 116, which is located on the intake side of air movement mechanism 112. Arranged before air movement mechanism 112 and filter 116 is an optional upstream, first or pre-ionizer 118, and arranged on the exhaust side of air movement mechanism 112 is an optional downstream, second, or post-ionizer 120. A flow of filtered air from the exhaust side of filter 116 exits air cleaning device housing 110 via an air exhaust port 122. Air cleaning device 100 further includes a flow chamber 124 that is preferably mechanically and fluidly connected to air cleaning device housing 110 in close proximity to air exhaust port 122, an odor elimination (OE) supply 126 disposed within flow chamber 124 such that a headspace 128 exists around OE supply 126, a metering orifice 130 that creates an airflow path between flow chamber 124 and air exhaust port 122, and a deflector 132 for directing airflow from flow chamber 124 into the air stream of filtered air exiting air exhaust port 122.

Air cleaning device housing 110 is representative of any lightweight plastic or metal enclosure for housing the elements of air cleaning device 100. Air cleaning device housing 110 is suitably sized and shaped for a tabletop air freshening device for home or office use. The footprint of air cleaning device housing 110 may be, for example, but is not limited to, rectangular, square, oval, or circular shape and of an area not more than, for example, 25 in$^2$. The height of air cleaning device housing 110 is, for example, 9.75 inches or less. An example of an air cleaning device housing 110 is described in more detail below in reference to FIG. 2.

Air movement mechanism 112 is, for example, in a preferred embodiment, a standard, commercially available axially mounted multi-speed AC or DC electric fan for moving air through filter 116. The filter 116 preferably has a volume of 9.85 in$^3$.

Air movement mechanism 112 is capable of providing, for example, 30-100 cubic feet/minute (CFM) of airflow. An example of a multi-speed AC electric fan is Sunon SP101-4F from Sunon, Inc. (Brea, Calif.). Those skilled in the art will appreciate that the power supply (not shown) and electronic control (not shown) of a standard, multi-speed AC or DC electric fan is well known. In an alternative embodiment, a squirrel cage fan may be used. In still another embodiment, the air movement mechanism 112 may be a fan impeller as described in U.S. Pat. No. 5,620,306, entitled, "Impeller." The '306 patent describes a pressure boost impeller configured for compressing fluids, such as gases and liquids. The impeller of the '306 patent has a front intake area, a rear discharge area, and a hub containing the rotational axis of the impeller. Several blades extend about the hub, with some of the blades being in an overlapping relationship, in order to define a passageway between adjacent blades. While the air movement mechanism or fan 112 is shown downstream the filter 116 in the figures provided, in another possible embodiment the fan may be on the opposite side of the filter or "upstream" of the filter.

In a preferred embodiment, filter 116 is an arresting filter that settles out particulates. For example, filter 116 is a small footprint filter that has a clean air delivery rate (CADR) rating of 80 or less, a pressure drop of less than 10-12 pascals, and an ozone emission of less than 0.005 ppm. CADR is an industry standard filter rating that is based on how much material is removed from the air by the filter over a predetermined period of time. Filter 116 includes a mesh that is fine enough to filter out the desired particulates. The finer the particle, the finer the mesh and, therefore, the greater the pressure needed to move air through the screen, which affects the possible CFM and the rate of air exchange in the room. In the case of air cleaning device 100, if, for example, air movement mechanism 112 provides approximately 70 CFM entering filter 116, approximately 55 CFM of airflow exits filter 116. Filter 116 is, for example, a conventional filter. In another embodiment, filter 116 may be designed to maintain a charge, such as a self-charging filter manufactured by 3M Company (St. Paul, Minn.) as described in reference to U.S. Pat. No. 6,589,317, entitled, "Structured surface filtration media array;" U.S. Pat. No. 6,471,746, entitled, "Electrofiltration process;" or U.S. Pat. No. 6,454,839 entitled, "Electrofiltration apparatus." In yet another embodiment, an external charging mechanism (not shown) may be linked to the filter 116 to artificially, directly charge the filter to enhance its capability. An example of such filter and charging mechanism is that found in the Enviracaire® air cleaners available from Kaz, Inc. (New York, N.Y.).

Pre-ionizer 118 and post-ionizer 120 are both optional and serve as precipitating filter mechanisms used to enhance the function of filter 116. Alternatively, additional ionizers may be present. Pre-ionizer 118 and post-ionizer 120 are, for example, standard, commercially available needle ionizers that use high voltage electricity to create negative electrons. These electrons flow along the length of a pointed spike, or needle, where they stream into the air and attract oxygen molecules. At this point, they become negative ions that attach themselves to airborne particles. When enough negative ions attach to a particle, it gets too heavy to float in the air and drops to the ground or other oppositely charged surface (a process known as agglomeration), which effectively removes it from the circulating air. An example needle ionizer is that found in IG-133A from Comtech Research, LLC (South Greenfield, Mo.). Those skilled in the art will appreciate that the power supply (not shown) and electronic control (not shown) of a standard needle ionizer device is well known. It is also well known that ionizer arrangements such as used in this device can substitute "brush-type" elements for conventional "needles". Additionally, it is optional for the system to include a "grounding" element or plate. This "plate" is a conductive element that is typically disposed in a single plane and insulated by an air space that is 360 degrees and equidistant to each individual needle (or brush) element. The preferred spacing and plate configuration is tailored to multiple elements including, but not limited to, power supply, material choices and ionizer configuration. The purpose of the "grounding plate" is to define the space in which the ion stream occurs thereby managing the occurrence of "stray" charges that can create electrostatic discharge (ESD) or a so-called "black wall effect". The grounding plate is preferably operably connected to the power supply.

Flow chamber 124 is preferably configured from a housing formed of, for example, molded plastic, into which compound or OE supply 126 is installed to be in fluid communication therewith. The fluid emitting mechanism or flow chamber 124 is a confined area for holding OE supply 126, but is not a tightly sealed area and is open to the ambient environment on preferably one side. OE supply 126 is any supply of odor elimination compound in the form of, for example, fluid, liquid, volatile gel, beads, powders, pumps (including mechanical and piezo-electric) and/or aerosols. As a first example, OE supply 126 is a liquid odor elimination compound in a bottle and wick arrangement, such as provided in the Glade® Oust® refill bottle supplied by SC Johnson & Son, Inc. (Racine, Wis.). As a second example, OE supply 126 is a volatile gel odor elimination compound, such as provided in the Glade® PlugIns® refill cartridge also supplied by SC Johnson & Son, Inc. The dispensing element of OE supply 126 (e.g., the wick of the Glade® Oust® refill or the porous film of the Glade® Plugins® refill cartridge) is disposed in the free space represented by headspace 128. By way of evaporation, the odor elimination compound of OE supply 126 is allowed to pass through metering orifice 130. The treated air is then directed by deflector 132 toward air exhaust port 122 within which it mixes with the filtered air stream exiting air exhaust port 122 of air cleaning device 100 and thereby provides an odor elimination treatment to the filtered air stream exiting air cleaning device 100. The combination of metering orifice 130 and deflector 132 provides a mechanism for controlling the level of odor elimination treatment delivered into the filtered air stream.

Alternatively, one of ordinary skill in the art would recognize that the OE compound in the supply 126 may be substituted with another compound such as an insect control compound. Such a compound could be an insect repellant or an insecticide.

The overall electric power for air cleaning device 100 may be supplied via battery power or via a power supply that is plugged into a standard household 110v or 220v AC outlet.

In operation, OE supply 126 containing a quantity of an odor elimination compound is installed within flow chamber 124 of air cleaning device 100. The user activates air cleaning device 100, whereby air movement mechanism 112, pre-ionizer 118, and post-ionizer 120 are activated. In doing so, ambient air is drawn into air cleaning device 100 via air intake port 114. Air movement mechanism 112 moves approximately 70 CFM of airflow into filter 116. Pre-ionizer 118 serves to remove particles from the airflow as air moves toward the intake side of filter 116. Filter 116 then performs an additional filtering operation by the precipitation or arresting of particulates that are not removed by the action of pre-ionizer 118. Alternatively, a trapping type filter may be used. Approximately 55 CFM of filtered air exits the exhaust side of filter 116 and, subsequently, passes by post-ionizer 120, which removes any additional particles remaining in the airflow, as a final air purification event. As a result, filtered air is directed past metering orifice 130 of flow chamber 124 and toward air exhaust port 122. As filtered air passes over metering orifice 130 at high velocity, the treated air within headspace 128 is drawn into the filtered air stream. This is because a low pressure is created within flow chamber 124 due to the velocity of the air stream passing by deflector 132 and metering orifice 130. The pressure differential between the inside of air cleaning device housing 110 and flow chamber 124 is caused by the Bernoulli effect (sometimes called the Venturi effect). This effect associates a decrease in fluid pressure with an increase in the fluid's velocity (speed). The air is ambient and is drawn into flow chamber 124 and is treated by the action of OE supply 126. As such, the air is then introduced into the filtered air stream exiting air exhaust port 122 of air cleaning device 100 via metering orifice 130. Alternatively, as a result, an odor elimination (OE) treatment is delivered along with clean air to the environment by air cleaning device 100.

Figure 2:
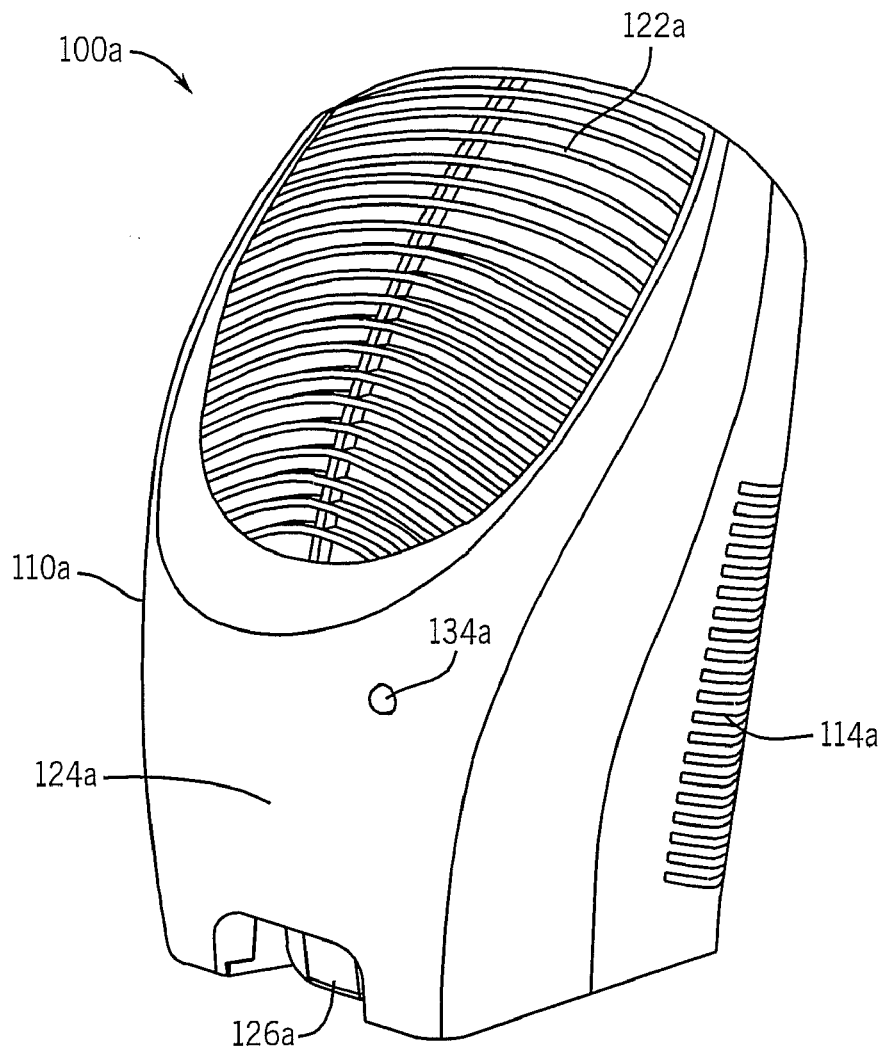
FIG. 2 illustrates a perspective view of an example physical implementation of the air cleaning device of FIG. 1.

FIG. 2 illustrates a perspective view of an example physical implementation of air cleaning device 100. More specifically, FIG. 2 illustrates a perspective view of an air cleaning device 100a in accordance with the invention. Air cleaning device 100a preferably includes a somewhat cylindrical shaped air cleaning device housing 110a that has a cross-sectional area of, for example, approximately 25 in$^2$. Air cleaning device 100a also preferably includes an air intake port 114a, an exhaust port 122a, a flow chamber 124a, an OE supply 126a, and optional indicator light 134a, e.g., to show the device is operating or to indicate for example the filter may need changing, or the supply has been depleted etc. Air intake port 114a, exhaust port 122a, flow chamber 124a and OE supply 126a are as described in reference to air intake port 114, exhaust port 122, flow chamber 124 and OE supply 126, respectively, of FIG. 1. Although not visible in FIG. 2, air movement mechanism 112, filter 116, pre-ionizer 118, post-ionizer 120, metering orifice 130, and deflector 132, as described in reference to FIG. 1, are housed within air cleaning device housing 110a of air cleaning device 100a.

In the example of air cleaning device 100a, air intake port 114a is located in a lower region of a sidewall of air cleaning device housing 110a and opposite to flow chamber 124a, which shows OE supply 126a installed therein in the form of a Glade® Oust® refill bottle, for example. Exhaust port 122a is located at the top of air cleaning device housing 110a and is slightly angled to provide both a vertical and horizontal directional flow of clean and treated air. Indicator light 134a includes a source of light, such as light-emitting diodes (LEDs), and indicates, for example, when the unit is in operation and/or when the filter and/or OE supply needs to be replaced. For example, the light may be green when the unit is in operation and red when the filter needs to be replaced. An optional fan control knob may also be included. This may be manipulated by the user to select the speed of air movement mechanism 112, which is, for example, a three-speed fan. Additionally, an optional treatment control knob may be included. This may be manipulated by the user to select the odor elimination level by adjusting the metering orifice 130. Flow chamber 124a for the OE supply 126a is disposed in a sidewall of air cleaning device housing 110a such that metering orifice 130 is fluidly coupled to exhaust port 122a with its filtered air stream passing there through to create the Bernoulli effect. In this way, treated ambient air, by the action of OE supply 126a, is introduced into the filtered air stream exiting air exhaust port 122a of air cleaning device 110a. A front grill and back grill are preferably present and preferably cover the intake and exhaust ports without significantly restricting air flow.

Figure 3:
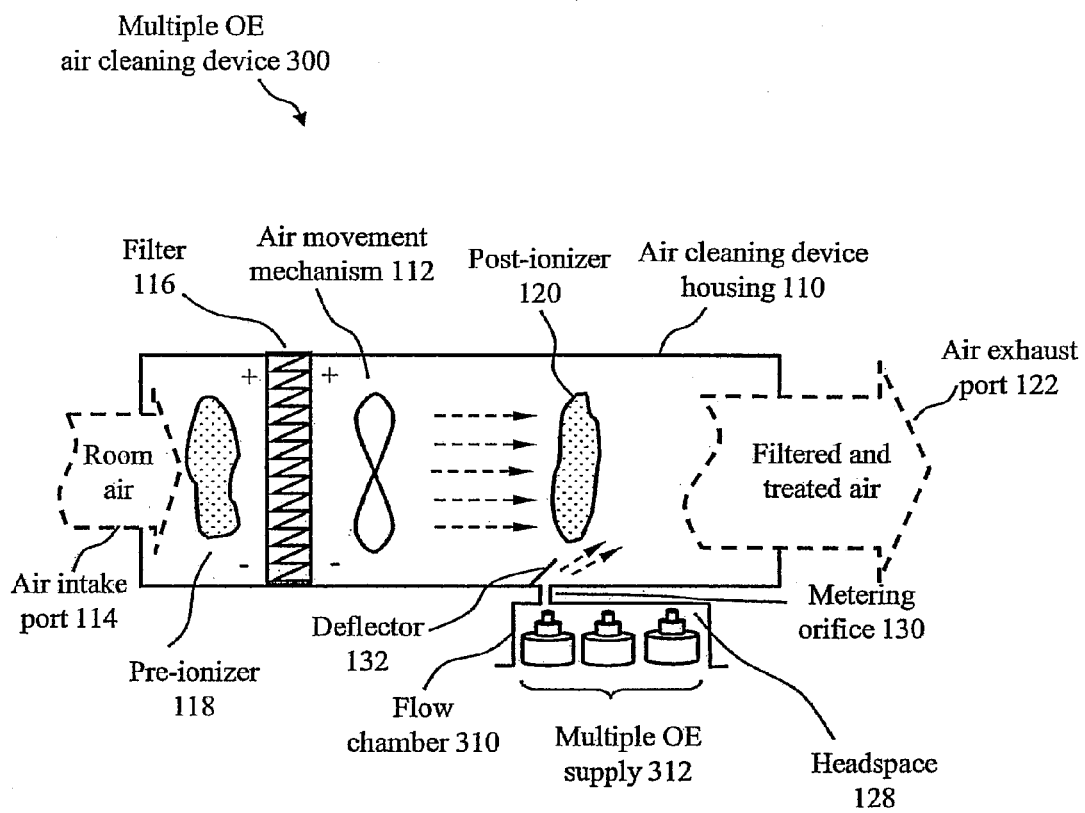
FIG. 3 is a functional diagram of a multiple OE air cleaning device that provides air purification in combination with a selection of odor elimination treatments in accordance with a second embodiment of the invention.

FIG. 3 is a functional diagram of a multiple OE air cleaning device 300 that provides air purification in combination with a selection of odor elimination treatments in accordance with a second embodiment of the invention. Multiple OE air cleaning device 300 of the present invention generally provides an odor elimination treatment to a room by entering an odor elimination compound into the filtered air exhaust stream of the device. Furthermore, multiple OE air cleaning device 300 of the present invention provides a selection of at least two odor elimination compounds each having a unique fragrance.

Multiple OE air cleaning device 300 includes air cleaning device housing 110, air movement mechanism 112, air intake port 114, filter 116, pre-ionizer 118, post-ionizer 120, air exhaust port 122, head space 128, metering orifice 130, and deflector 132, as described in reference to FIG. 1. Multiple OE air cleaning device 300 further includes a flow chamber 310 that is preferably mechanically and fluidly connected to air cleaning device housing 110 in close proximity to air exhaust port 122, and a multiple OE supply 312 disposed within flow chamber 310 such that headspace 128 exists around multiple OE supply 312. Flow chamber 310 differs from flow chamber 124 of air cleaning device 100 in that it is sized to accommodate a selection of at least two odor elimination compounds that form multiple OE supply 312, wherein each odor elimination compound has a unique fragrance. The multiple OE supply 312 may involve a capillary system (with liquid and wicks), a membrane/film system (with volatile gels), beads, powders, pumps (mechanical and/or piezo-electric), aerosols, etc.

An example of a capillary system with liquid and wicks is found in FIGS. 4A through 4E.

Figure 4A:
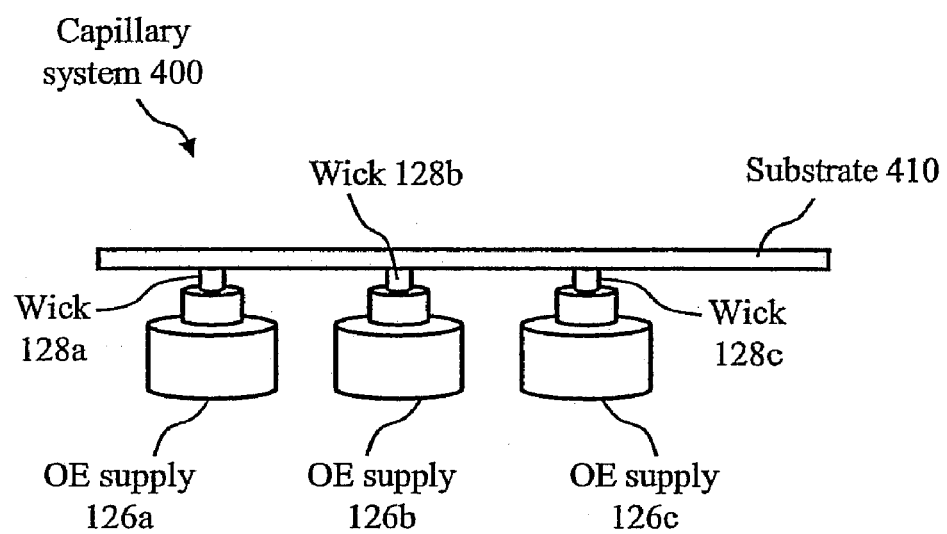
FIG. 4A illustrates a side view of a capillary system for providing a selection of odor elimination compounds for use in the multiple OE air cleaning device of FIG. 3.

FIG. 4A illustrates a side view of a capillary system 400 for providing a selection of odor elimination compounds in accordance with an example embodiment of multiple OE supply 312 of multiple OE air cleaning device 300. Additionally, FIGS. 4B, 4C, 4D, and 4E illustrate top views of capillary system 400 in four example operative positions, respectively. Capillary system 400 is formed of a wick-based system that incorporates a capillary member for delivering an odor elimination compound to the airflow. In this example and with reference to FIGS. 4A, 4B, 4C, 4D, and 4E, capillary system 400 includes an elongated, thin, flat substrate 410 formed of, for example, molded plastic or glass.

The shape of flat substrate 410 is not limited to that shown in FIGS. 4A, 4B, 4C, 4D, and 4E; flat substrate 410 may be, for example, rectangular shaped, square shaped, disk shaped, or cylindrical shaped. Arranged along the lower surface of substrate 410 are one or more capillary regions 412 (shown in FIG. 4B through FIG. 4E, but not visible in FIG. 4A) associated with one or more OE supplies 126, respectively. Each OE supply 126 further includes a wick 128, which is positioned in direct contact with the lower surface of substrate 410.

Capillary regions 412 are representative of a wickable surface for enhancing vaporization of the odor elimination compound into the air stream of multiple OE air cleaning device 300. Capillary regions 412 are, for example, 1 to 2 in$^2$ in area and are formed by one or more exposed capillary pathways (i.e., mechanical grooves) that are printed, etched, or molded into the surface of substrate 410. The critical characteristics of the capillary pathways may be optimized to the surface tension of specific odor elimination compounds. These characteristics include, for example, the angle of the groove walls, the sharpness of the lower corner, and a minimum depth specification.

In a preferred embodiment, capillary regions 412 are formed according to the principles described in Patent Application No. 20040074982 entitled "Wick-based delivery system with wick having small porosity sections," Patent Application No. 20040065750 entitled "Wick-based delivery system with wick having sections of varying porosities," and Patent Application No. 20040065749 entitled "Wick-based delivery system with wick made of different composite materials" all assigned to SC Johnson & Son, Inc. (Racine, Wis.), which are incorporated herein by reference. The above-cited patent applications describe an evaporative device that includes a container for holding a liquid that has a porous wick extending through an opening, such that a portion of the wick contacts the liquid held within the container and a portion of the wick is exposed to the ambient environment, wherein the wick transfers the liquid from the container to the ambient air, and a portion of the wick is in communication with a surface of a capillary member. The surface has one or more exposed capillary pathways along which liquid, transferred by the wick from the container, is drawn by capillary action for dispersion to the ambient air.

An example of a wick-based OE supply suitable for use as OE supply 126 is the Glade® Oust® refill bottle. Each OE supply 126 may also preferably include a fragrance element within its odor elimination compound. Example fragrances include cinnamon, apple, citrus, vanilla, floral fragrances, and tropical fruit fragrances.

With continuing reference to FIGS. 4A, 4B, 4C, 4D, and 4E, wicks 128a, 128b, and 128c of the fluid emitting or OE supplies 126a, 126b, and 126c, respectively, may be arranged linearly and in contact with the lower surface of substrate 410. A capillary region 412a is associated with wick 128a, a capillary region 412b is associated with wick 128b, and a capillary region 412c is associated with wick 128c. Only one wick 128 at a time is in contact with and, therefore, engaged with, its associated capillary region 412. This is accomplished by the user adjusting the relative position of substrate 410 to OE supplies 126a, 126b, and 126c (and wicks 128a, 128b, and 128c), either by holding OE supplies 126a, 126b, and 126c stationary and moving substrate 410 or by holding substrate 410 stationary and moving OE supplies 126a, 126b, and 126c. The former will be described herein.

Figure 4B:
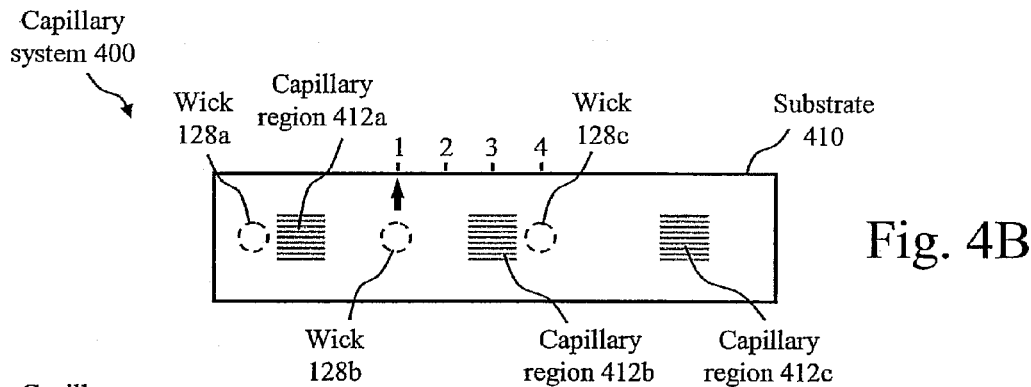
FIGS. 4B, 4C, 4D, and 4E illustrate top views of the capillary system of FIG. 4A in four example operative positions, respectively.
Figure 4C:
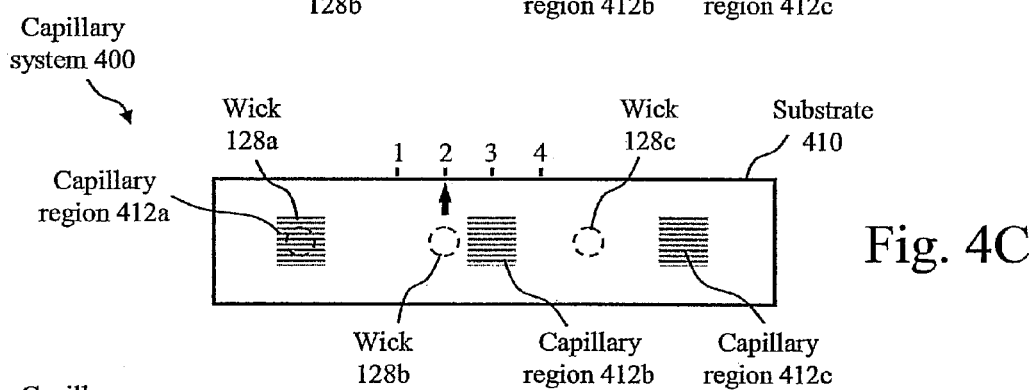
Figure 4D:
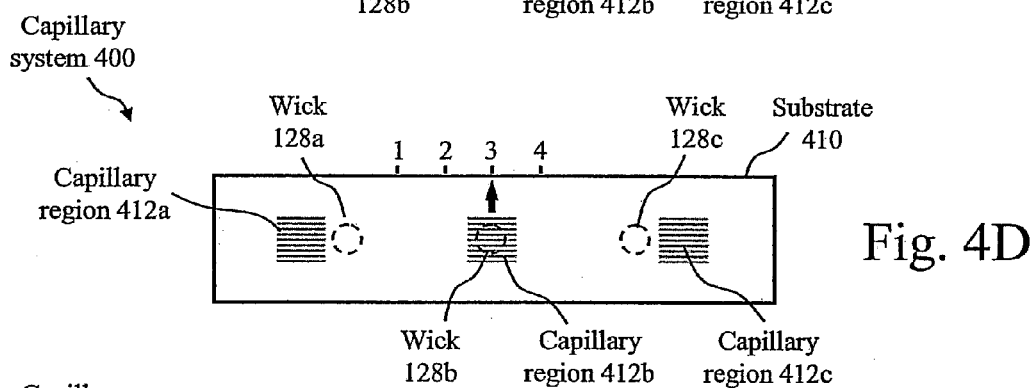
Figure 4E:
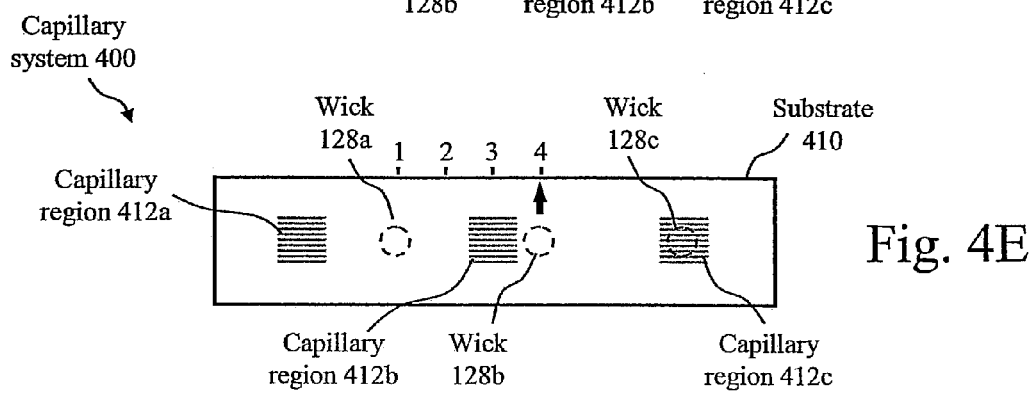

Substrate 410 may be slideably installed within flow chamber 310 of multiple OE air cleaning device 300 and aligned with and in contact with wicks 128a, 128b, and 128c of OE supplies 126a, 126b, and 126c, respectively, which are also installed within flow chamber 310. FIG. 4B illustrates a first position, wherein none of wicks 128a, 128b, or 128c is engaged with its associated capillary regions 412a, 412b or 412c, respectively, and, thus, no odor elimination treatment is selected, which thereby provides a means for the user to turn off the odor elimination treatment within multiple OE air cleaning device 300. FIG. 4C illustrates a second position, wherein wick 128a is engaged with capillary region 412a and wicks 128b and 128c are not engaged with capillary regions 412b and 412c, respectively, and, thus, the odor elimination treatment of OE supply 126a is selected. FIG. 4D illustrates a third position, wherein wick 128b is engaged with capillary region 412b and wicks 128a and 128c are not engaged with capillary regions 412a and 412c, respectively, and, thus, the odor elimination treatment of OE supply 126b is selected. Finally, FIG. 4E illustrates a fourth position, wherein wick 128c is engaged with capillary region 412c and wicks 128a and 128b are not engaged with capillary regions 412a and 412b, respectively, and, thus, the odor elimination treatment of OE supply 126c is selected. This example odor elimination treatment selection is summarized in Table 1 below.

TABLE 1

First example odor elimination treatment selection of capillary system 400

| Position | Treatment mode |
| --- | --- |
| 1 | No treatment selected |
| 2 | Treatment #1 selected |
| 3 | Treatment #2 selected |
| 4 | Treatment #3 selected |

In operation, in the second, third, and fourth positions, as air flows across the surface of substrate 410 and, thus, across capillary regions 412a, 412b, and 412c, the liquid is transferred by wicks 128a, 128b, or 128c, respectively, from OE supplies 126a, 126b, or 126c, respectively, and drawn by the capillary action of capillary regions 412a, 412b or 412c, respectively, for dispersion by evaporation to the ambient air within flow chamber 310 and subsequently drawn into the filtered air stream via metering orifice 130. The filtered and treated air exits multiple OE air cleaning device 300 via air exhaust port 122. The user may select the positions manually by manipulating substrate 410 relative to OE supplies 126. Alternatively, a standard motion control system (not shown) may be provided in combination with capillary system 400 and, thus, the user uses electronic control to select the desired fragrance. For example, the user controls the motion control system by use of a numbered dial or a push-button for scrolling through the various treatment selections.

In an alternative embodiment, capillary regions 412 may be designed such that changing their position relative to wicks 128 provides contact with fewer or more capillary pathways, which thereby provides a way to adjust the treatment level. For example, a "high" treatment level setting, a "medium" treatment level setting, and a "low" treatment level setting may be provided by adjusting the wick content area and the capillary groove spacing. This example odor elimination treatment selection is summarized in Table 2 below.

TABLE 2

Second example odor elimination treatment selection of capillary system 400

| Position | Treatment mode |
| --- | --- |
| 1 | No treatment selected |
| 2 | Treatment #1 - low level |
| 3 | Treatment #1 - medium level |
| 4 | Treatment #1 - high level |
| 5 | Treatment #2 - low level |
| 6 | Treatment #2 - medium level |
| 7 | Treatment #2 - high level |
| 8 | Treatment #3 - low level |
| 9 | Treatment #3 - medium level |
| 10 | Treatment #3 - high level |

In yet another alternative embodiment, capillary system 400 may be designed to optionally provide a blend of treatments. This may be accomplished, for example, by (1) providing a layout of capillary regions 412 on substrate 410 such that two OE supplies 126 may be engaged at the same time with a single common capillary region 412, thereby blending the two treatments by use of the shared capillary region 412, or (2) providing a layout of capillary regions 412 on substrate 410 such that two OE supplies 126 may be engaged at the same time with their own independent capillary regions 412, which allows the two treatments to blend in the surrounding ambient air within headspace 128 of flow chamber 310 and then blended air passes through metering orifice 130 and into the filtered air stream. This example odor elimination treatment selection is summarized in Table 3 below.

TABLE 3

Third example odor elimination treatment selection of capillary system 400

| Position | Treatment mode |
|---|---|
| 1 | No treatment selected |
| 2 | Treatment #1 selected |
| 3 | Blend of treatment #1 and #2 selected |
| 4 | Treatment #2 selected |
| 5 | Blend of treatment #2 and #3 selected |
| 6 | Treatment #3 selected |
| 7 | Blend of treatment #3 and #1 selected |

Multiple OE air cleaning device 300 is not limited to the above-mentioned example combinations. Those skilled in the art will appreciate that multiple OE air cleaning device 300 may be designed with a capillary system that provides any number of combinations of treatment levels and treatment blends.

With reference to FIGS. 4A through 4E and all embodiments of multiple OE supply 312 within multiple OE air cleaning device 300, such as capillary system 400, membranes/films, beads, powders, pumps and/or aerosols, the selection of one of the multiple treatments or no treatment at all may be performed via manual manipulation of the elements of multiple OE supply 312 by the user. Alternatively, a standard motion control system (not shown) may be provided within multiple OE air cleaning device 300. There the user selects with the electronic control the desired mode. The inclusion of a motion control system within multiple OE air cleaning device 300 also allows the unit to be timer controlled. For example, multiple OE air cleaning device 300 may include well-known electronics (not shown) that allows the user to select when multiple OE air cleaning device 300 is automatically turned on or off and also to automatically select a given treatment at a given time of day for a given amount of time, all under automatic control. Further, it is a known phenomenon that the users' senses become saturated, or deadened, to a specific fragrance if exposed to that fragrance for a constant duration. Therefore, a specific timing sequence allows for multiple OE air cleaning device 300 to initiate a wait period, with no odor elimination, before aligning capillary region 412 with a different wick 128 of a different OE supply 126.

Furthermore, with reference to FIGS. 4A through. 4E and all embodiments of multiple OE supply 312 within multiple OE air cleaning device 300, such as capillary system 400, membranes/films, beads, powders, pumps and/or aerosols, the physical assembly forming multiple OE supply 312 is easily removable from multiple OE air cleaning device 300, such that the user can easily and conveniently replace the odor elimination compound when it is depleted.

Figure 5:
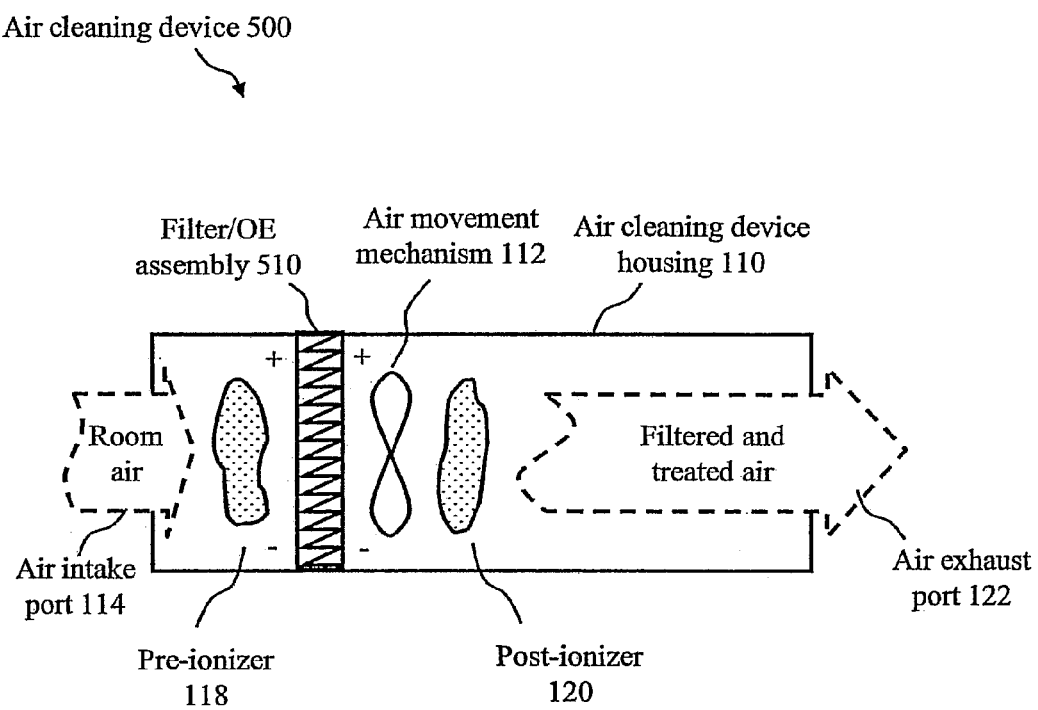
FIG. 5 is a functional diagram of an air cleaning device that provides air purification in combination with odor elimination in accordance with a third embodiment of the present invention.

FIG. 5 is a functional diagram of an air cleaning device 500 that provides air purification in combination with odor elimination in accordance with a third embodiment of the invention. Air cleaning device 500 of the present invention generally provides an odor elimination treatment to a room by entering an odor elimination compound into the filtered air exhaust stream of the device.

Air cleaning device 500 includes air cleaning device housing 110, air movement mechanism 112, air intake port 114, pre-ionizer 118, post-ionizer 120, and air exhaust port 122, as described in reference to FIG. 1. Air cleaning device 500 further includes a filter/OE assembly 510 disposed between pre-ionizer 118 and air movement mechanism 112. Filter/OE assembly 510 differs from filter 116 of air cleaning device 100 in that an odor elimination mechanism is integrated directly with the filter mechanism and, thus, a separate flow chamber 124 and OE supply 126, as shown in air cleaning device 100 of FIG. 1, are not needed. More details of example embodiments of filter/OE assembly 510 are found in reference to FIGS. 6A and 6B.

Figure 6A:
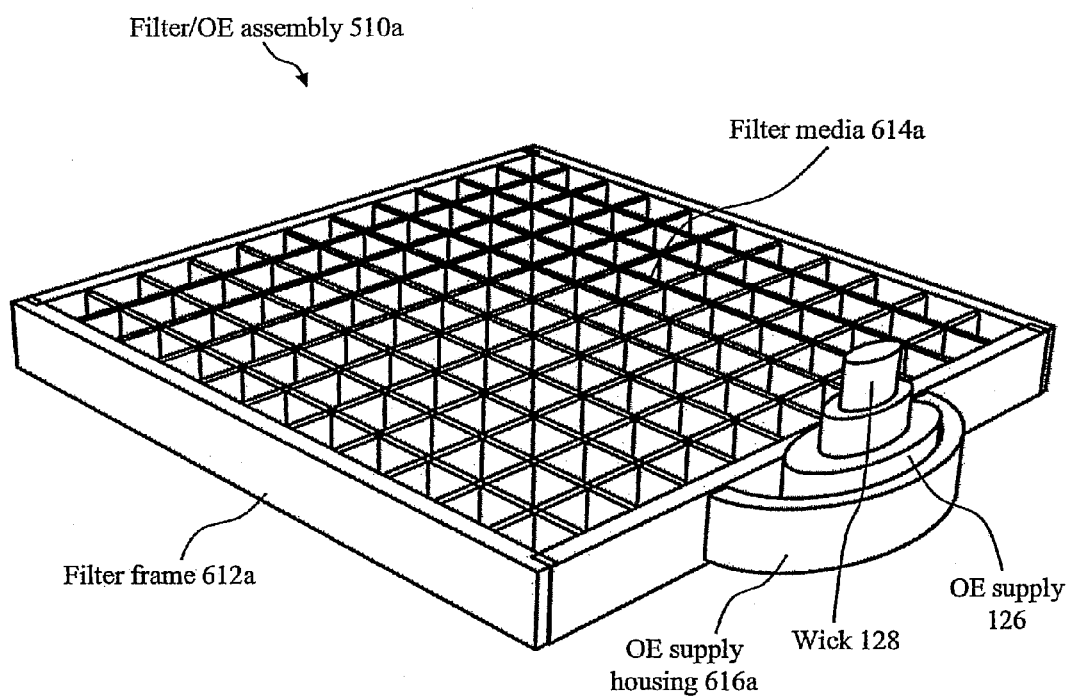
FIG. 6A illustrates a perspective view of a first example physical implementation of a filter/OE assembly for use in the air cleaning device of FIG. 5.

FIG. 6A illustrates a perspective view of a first example physical implementation of filter/OE assembly 510. More specifically, FIG. 6A illustrates a perspective view of a filter/OE assembly 510a for providing an odor elimination mechanism that is integrated directly into a filter mechanism in accordance with the invention.

Filter/OE assembly 510a includes a filter frame 612a, which houses a filter media 614a for eliminating particulates, such as manufactured by 3M Company (St. Paul, Minn.). Filter media 614a is permanently affixed within filter frame 612a or, alternatively, filter media 614a is slideably affixed within filter frame 612a such that filter media 614a may be removed and filter frame 612a may be reused or replaced. Preferably attached to filter frame 612a is an OE supply housing 616a for holding at least one OE supply 126 that has a wick 128, such as the Glade® Oust® refill bottle. Filter frame 612a and OE supply housing 616a are formed of any rigid lightweight material, such as molded plastic. Preferably, a quantity of liquid odor elimination compound within OE supply 126 is provided such that the time it takes the liquid to be consumed is approximately equal to the expected lifetime of filter media 614a. In this way, both OE supply 126 and filter media 614a may be serviced and/or replaced at the same time.

In this example, because OE supply 126 is wick-based supply that contains a liquid odor elimination compound, filter/OE assembly 510a has a specific orientation within air cleaning device housing 110 of air cleaning device 500 to ensure proper operation thereof. In particular, when installed, wick 128 of OE supply 126 is located on the exhaust side of filter/OE assembly 510a and within a cavity (not shown) that has a metering mechanism (not shown) such that low pressure is created by filtered air passing rapidly thereby. The odor elimination compound emitting from wick 128 of OE supply 126 is drawn into the filtered air stream preferably via a manifold or passageway because of the Bernoulli effect, as described in FIG. 1. In this way, an odor elimination treatment is introduced into the filtered air stream and, thus, filtered and treated air exits exhaust port 122 of air cleaning device 500 and is delivered to the environment.

Figure 6B:
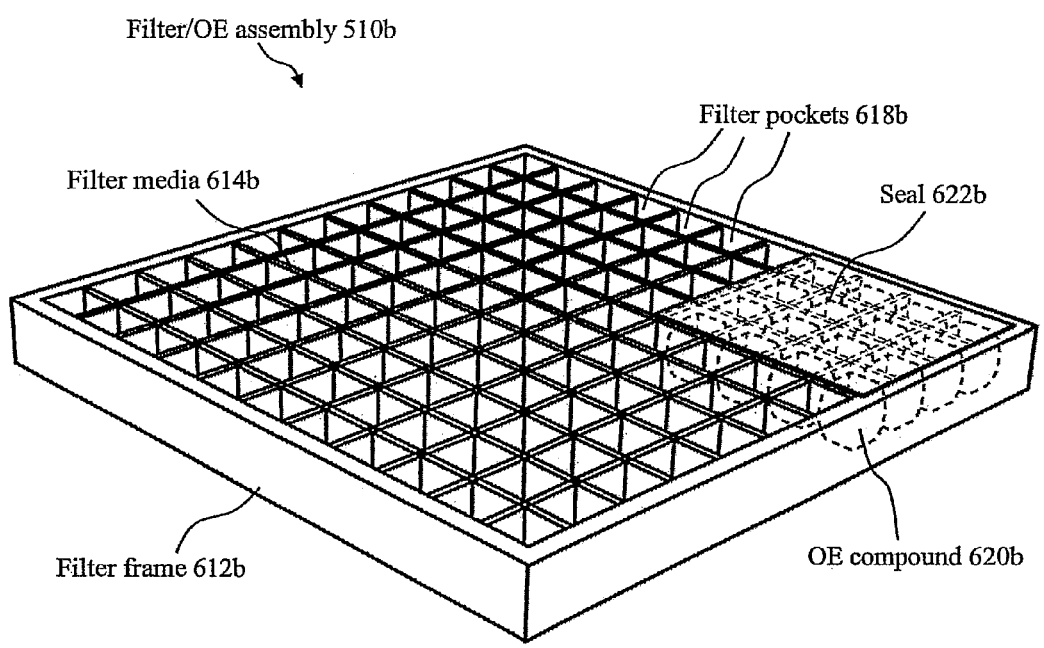
FIG. 6B illustrates a perspective view of a second example physical implementation of a filter/OE assembly for use in the air cleaning device of FIG. 5.

FIG. 6B illustrates a perspective view of a second example physical implementation of filter/OE assembly 510. More specifically, FIG. 6B illustrates a perspective view of a filter/OE assembly 510b for providing an odor elimination mechanism that is integrated directly into a filter mechanism in accordance with the invention.

Filter/OE assembly 510b includes a filter frame 612b, which houses a filter media 614b for precipitating particulates, such as manufactured by 3M Company (St. Paul, Minn.). Filter media 614b is permanently affixed within filter frame 612b or, alternatively, filter media 614b is slideably affixed within filter frame 612b such that filter media 614b may be removed and filter frame 612b is reused. Furthermore, filter media 614b typically has a pleated, corrugated, or honeycomb structure and, thus, includes a plurality of filter pockets 618b that are formed over its entire area. FIG. 6B shows that some number of filter pockets 618b within filter media 614b that have a dispersion mechanism for a compound. For example, the filter pockets may be filled with an OE compound 620b, while some larger number of filter pockets 618b within filter media 614b are empty of OE compound 620b.

In a first example, OE compound 620b is a volatile gel, such as the volatile gel that is used within Glade® PlugIns® refill cartridge. A seal 622b is placed on the surface of filter media 614b covering only the filter pockets 618b that contain OE compound 620b. In the case of a volatile gel, seal 622b is a multilayer structure such as that used within Glade® PlugIns® refill cartridge within which, upon use, an outer foil seal is pealed away to expose a porous film that serves to meter out OE compound 620b at a predetermined rate.

In a second example, OE compound 620b is a plurality of wicks that are sized to be individually press-fitted into filter pockets 618b. Each wick is impregnated with a liquid odor elimination compound, such as used within the Glade® Oust® refill bottle. Again, a seal 622b is placed on the surface of filter media 614b covering only the filter pockets 618b that contain OE compound 620b. Upon use, seal 622b is pealed away to expose OE compound 620b, which allows the liquid contained in the wick material to be dispensed by evaporation.

OE compound 620b is located on the exhaust side of filter/OE assembly 510b and within a cavity (not shown) that has a metering mechanism (not shown) such that low pressure is created by filtered air passing rapidly thereby. The odor elimination compound emitting from OE compound 620b is drawn into the filtered air stream because of the Bernoulli effect, as described in FIG. 1. The quantity of filter pockets 618b within filter media 614b that are empty of OE compound 620b are performing the air filtering function. In this way, an odor elimination treatment is introduced into the filtered air stream. Thus, filtered and treated air exits exhaust port 122 of air cleaning device 500 and is delivered to the environment. Preferably, a quantity of OE compound 620b within filter pockets 618b is provided such that the time it takes OE compound 620b to be consumed is approximately equal to the expected lifetime of filter media 614b.

Figure 7:
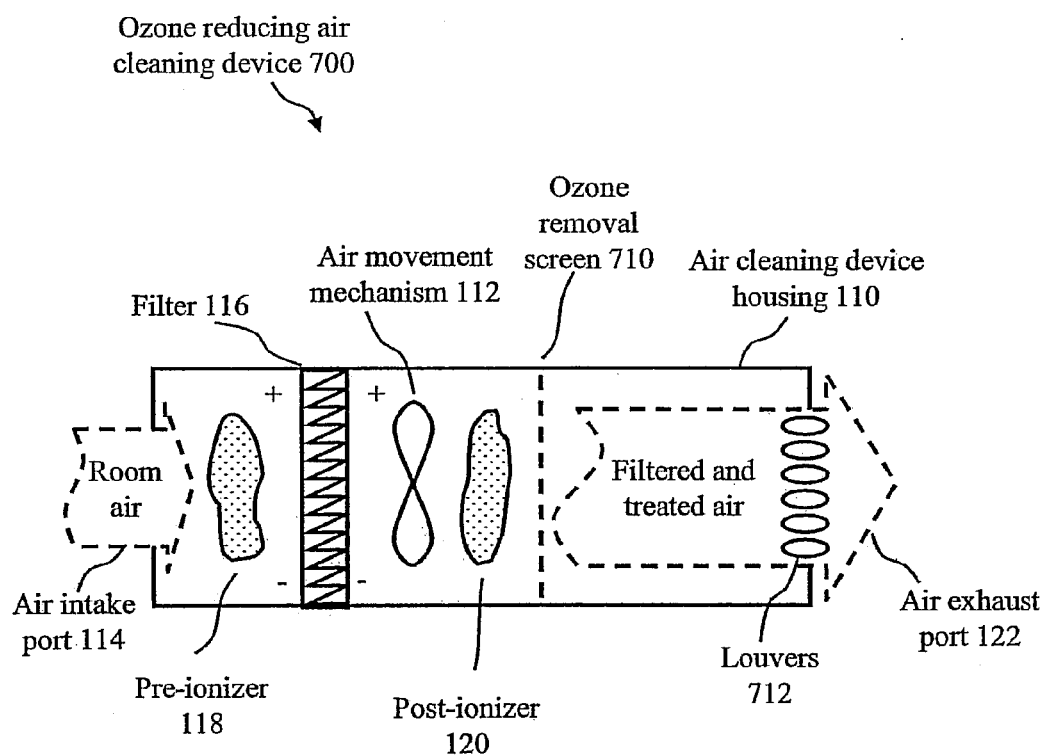
FIG. 7 is a functional diagram of an ozone reducing air cleaning device that provides air purification in combination with ozone reduction in accordance with a fourth embodiment of the invention.

FIG. 7 is a functional diagram of an ozone reducing air cleaning device 700 that provides air purification in combination with ozone reduction in accordance with a fourth embodiment of the invention. Ozone reducing air cleaning device 700 of the present invention generally provides an ozone reduction treatment to a room by applying a coating to the elements of the device. This coating serves to scrub the ozone out of the air stream of an air purification unit.

Ozone reducing air cleaning device 700 includes air cleaning device housing 110, air movement mechanism 112, air intake port 114, filter 116, pre-ionizer 118, post-ionizer 120, and air exhaust port 122, as described in reference to FIG. 1. Ozone reducing air cleaning device 700 further includes an ozone removing chemical that is applied to a screen-like member 710 and disposed between the post-ionizer 120 and air exhaust port 122.

FIG. 7 also shows an optional set of louvers 712, which represents openings within air cleaning device housing 110 that form air exhaust port 122.

Ozone removal screen 710 is a mesh screen coated with a commercially available ozone scrubbing substance, such as PremAir® catalysts from Engelhard Corporation (Iselin, N.J.). The mesh of ozone removal screen 710 is suitably porous such that it does not restrict the flow rate of the filtered air stream. In addition to or instead of the coated ozone removal screen 710, surfaces of all elements of ozone reducing air cleaning device 700 that are present within the airflow channel between air intake port 114 and air exhaust port 122 may also be coated with the above-mentioned ozone scrubbing substance or catalyst. For example, the inner surfaces of air cleaning device housing 110, the surface of any fan blades associated with air movement mechanism 112, and the surfaces of optional louvers 712 may be coated. In addition, most catalyst-style removal agents perform more effectively when heated. The air cleaning device 700 incorporates a molded surface that achieves a temperature rise greater than ambient conditions during unit operation thereby delivering a more effective use of the ozone scrubbing compound. The selected surface becomes heated by absorbing thermal energy from normal motor/fan operation.

Ozone removal can be also accomplished by other means including treating the air flow with specialized compounds, e.g., volafiles. Technologies such as "Nozone" can be delivered using a device and refill system as defined by cleaning device 700 and OE supply 126.

In operation, ozone reducing air cleaning device 700 performs an air purification process as described in reference to air cleaning device 100 of FIG. 1. Additionally, ozone that is present within the ambient air entering intake port 114 and ozone that is generated by pre-ionizer 118 and post-ionizer 120 during the air purification process is reduced by the action of air passing through ozone removal screen 710 and passing over the surfaces of ozone reducing air cleaning device 700 which are coated with the ozone scrubbing substance. In this way, ozone reducing air cleaning device 700 allows for use of an air cleaning device with an ionizer without increasing the level of ozone in the ambient air.

Those skilled in the art will recognize that the ozone reduction mechanism as described in reference to ozone reducing air cleaning device 700 of FIG. 7 may by used in combination with any of the odor elimination treatment mechanisms described in reference to FIGS. 1 through 6B.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. In addition, the individual components need not be fabricated from the disclosed materials, but could be fabricated from virtually any suitable materials.

Moreover, the individual components need not be formed in the disclosed shapes, or assembled in the disclosed configuration, but could be provided in virtually any shape, and assembled in virtually any configuration. Further, although several components are described herein is a physically separate module, it will be manifest that the may be integrated into the apparatus with which it is associated. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

What is claimed is:

1. An air purification system including:
   a housing;
   a filter operatively communicating with the housing;
   a first ionizer in communication with the housing;
   an air movement mechanism for directing airflow through the housing;
   a fluid emitting mechanism within the housing in fluid communication with the airflow from the air movement mechanism that has a plurality of fluid reservoirs arranged in contact with a substrate that can selectively contact one or more of the plurality of fluid reservoirs; and
   a second ionizer in fluid communication with the air movement mechanism.

2. The system of claim 1 wherein the fluid emitting mechanism is an odor elimination mechanism.

3. The system of claim 1 further comprising:
   a front grill plate operatively attached to the housing;
   a back grill plate operatively attached to the housing; and
   an airflow channel through the housing which brings air in through the back grill plate and pushes air out through the front grill plate.

4. The system of claim 1 wherein the filter has an electrostatic charge and has a means for indicating that the filter should be replaced.

5. The system of claim 1 wherein the filter has a volume of 9.85 in$^3$.

6. The system of claim 1 wherein the filter is in operable communication with a fan; and wherein filtered air is then directed by a deflector toward an air exhaust port and wherein the deflection by the deflector further mixes the filtered air exiting an air exhaust port with an odor elimination treatment.

7. The system of claim 1 further comprising:
   an odor elimination supply to introduce a compound into a filtered airflow of the system; and
   wherein the filter is an arresting filter that settles particulates out of the airflow and maintains a charge;
   wherein air movement mechanism provides approximately 70 CFM of airflow entering filter approximately 55 CFM of airflow exiting the filter.

8. The system of claim 1 wherein the filter is charged by an external charging mechanism to enhance its capability.

9. The system of claim 1 wherein at least one of the ionizers is a brush-type ionizer.

10. The system of claim 1 wherein at least one of the ionizers is a needle ionizer.

11. The system of claim 1 further comprising a grounding surface operably attached to the power supply.

12. The system of claim 1 further comprising a supply having an air purification liquid in a bottle and wick arrangement.

13. The system of claim 1, wherein at least two odor elimination (OE) compounds are supplied to form an OE supply, wherein each compound has a unique fragrance; and wherein the OE supply involves a capillary system with at least one of: a liquid and wick; a membrane system with volatile gels, beads, and powders; a pump; and aerosols.

14. An air cleaning device comprising;
   a housing having an inner housing cavity;
   an air intake port in fluid communication with the inner cavity of the housing;
   an upstream ionizer in fluid communication with the air intake port;
   a filter after the upstream ionizer;
   an air movement mechanism after the filter;
   a downstream ionizer within the cavity;
   a flow chamber connected to the cavity having a head space and a metering orifice in fluid communication with the head space and the cavity;
   an odor elimination supply having a plurality of odor elimination compounds, and a selector that is selectively engaged with one or more of the plurality of odor elimination compounds and is in fluid communication with the flow chamber;
   a deflector within the cavity to deflect flow of odor elimination material from the flow chamber;
   an air exhaust port in fluid communication with the cavity.

15. An air cleaning device comprising;
   a housing having a first port for intaking air from a room, an inner cavity in fluid communication with the first port, and a second port in fluid communication with the inner cavity;
   a mechanism for ionizing air that enters the first port;
   a filter for filtering air within the cavity;
   an air movement mechanism drawing air through the cavity;
   a chamber for introducing a flow of an odor elimination material from an odor elimination supply having two or more odor elimination compounds and a selector that is selectively engaged with one or more of the plurality of odor elimination compounds to a head space in through a orifice that controls the flow into the cavity; and
   a second mechanism for ionizing the air within the cavity;
   wherein filtered and treated air is exhausted through the second port.

16. An air purification system including:
   a housing;
   a filter operatively communicating with the housing;
   a first ionizer in communication with the housing;
   an air movement mechanism for directing airflow through the housing;
   a second ionizer in fluid communication with the air movement mechanism,
   an odor elimination (OE) compound in a supply;
   a light to indicate the filter needs changing or the OE supply has been depleted;
   a metering orifice and a deflector to provide a mechanism for controlling a level of odor elimination treatment delivered into a filtered air stream; and
   a treatment control knob manipulated by a user to select an odor elimination level by adjusting the metering orifice.

17. An air purification system including:
   a housing;
   a filter operatively communicating with the housing;
   a first ionizer in communication with the housing;
   an air movement mechanism for directing airflow through the housing;
   a second ionizer in fluid communication with the air movement mechanism;
   a fluid emitting supply that has a plurality of bottles arranged linearly and in contact with a substrate; and
   wherein the filter is a filter media that is slideably affixed within a filter frame such that the filter media is removable and the filter frame is reusable.

* * * * *